(12) United States Patent
Vunjak-Novakovic et al.

(10) Patent No.: US 11,261,413 B2
(45) Date of Patent: Mar. 1, 2022

(54) BIOREACTOR SYSTEM FOR ENGINEERING TISSUES

(71) Applicant: The Trustees of Columbia University in the City of New York, New York, NY (US)

(72) Inventors: Gordana Vunjak-Novakovic, New York, NY (US); Keith Yeager, Jersey City, NJ (US); Kacey Ronaldson, New York, NY (US); Stephen Ma, New York, NY (US); Timothy Chen, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 477 days.

(21) Appl. No.: 16/246,007

(22) Filed: Jan. 11, 2019

(65) Prior Publication Data

US 2019/0276785 A1    Sep. 12, 2019

Related U.S. Application Data

(63) Continuation of application No. PCT/US2017/041996, filed on Jul. 13, 2017.

(Continued)

(51) Int. Cl.
*C12M 3/00* (2006.01)
*C12M 1/32* (2006.01)
(Continued)

(52) U.S. Cl.
CPC .............. *C12M 21/08* (2013.01); *C12M 1/34* (2013.01); *C12M 23/12* (2013.01); *C12M 23/16* (2013.01);
(Continued)

(58) Field of Classification Search
None
See application file for complete search history.

(56) References Cited

U.S. PATENT DOCUMENTS

| 6,218,182 B1 | 4/2001 | Naughton et al. |
| 6,979,308 B1 | 12/2005 | MacDonald et al. |

(Continued)

FOREIGN PATENT DOCUMENTS

| WO | 2013184527 | 12/2013 |
| WO | 2014085933 | 6/2014 |

(Continued)

OTHER PUBLICATIONS

Sebastian Schaaf, Aya Shibamiya, Marco Mewe, Alexandra Eder, Andrea Stöhr, Marc N. Hirt, Thomas Rau, Wolfram-Hubertus Zimmermann, Lenard Conradi, Thomas Eschenhagen, Arne Hansen, Human Engineered Heart Tissue as a Versatile Tool in Basic Research and Preclinical Toxicology, PLoS ONE Oct. 20, 2011 6(10): e26397, https://doi.org/10.1371/journal.pone.0026397.

(Continued)

*Primary Examiner* — William H. Beisner
(74) *Attorney, Agent, or Firm* — Reed Smith LLP; Lisa A. Chiarini

(57) ABSTRACT

A bioreactor is provided that permits engineering of multiple different tissues. The bioreactor has a series of flow paths that permit application of tissue-specific media while simultaneously innervating the various different tissues with a common media. The flow paths for the various medias are designed to prevent mixing of the various media as they simultaneously innervate the tissue.

12 Claims, 16 Drawing Sheets

Related U.S. Application Data

(60) Provisional application No. 62/361,648, filed on Jul. 13, 2016.

(51) Int. Cl.
  *C12M 3/06* (2006.01)
  *C12M 1/00* (2006.01)
  *C12M 1/42* (2006.01)
  *C12M 1/34* (2006.01)
  *C12Q 1/02* (2006.01)
  *G01N 33/50* (2006.01)

(52) U.S. Cl.
  CPC ............ *C12M 23/44* (2013.01); *C12M 29/04* (2013.01); *C12M 35/02* (2013.01); *C12Q 1/02* (2013.01); *G01N 33/50* (2013.01)

(56) References Cited

U.S. PATENT DOCUMENTS

| | | | |
|---|---|---|---|
| 7,198,940 B2 | 4/2007 | Vellinger et al. | |
| 7,604,987 B2 | 10/2009 | Hutmacher et al. | |
| 8,492,140 B2 | 7/2013 | Smith et al. | |
| 2004/0132184 A1 | 7/2004 | Dennis et al. | |
| 2010/0112690 A1* | 5/2010 | Eddington | C12M 23/12 435/374 |
| 2014/0094388 A1 | 4/2014 | Wakatsuki | |
| 2015/0313704 A1* | 11/2015 | Thavandiran | C12M 25/00 623/23.72 |
| 2016/0282338 A1* | 9/2016 | Miklas | C12M 23/12 |

FOREIGN PATENT DOCUMENTS

| | | |
|---|---|---|
| WO | 2014201254 | 12/2014 |
| WO | 2015054383 | 4/2015 |
| WO | 2015061907 | 5/2015 |
| WO | 2015084168 | 6/2015 |

OTHER PUBLICATIONS

Caspi O, Lesman A, Basevitch Y, Gepstein A, Arbel G, Habib IH, Gepstein L, Levenberg S., Tissue Engineering of Vascularized Cardiac Muscle from Human Embryonic Stem Cells, Circulation Research Jan. 11, 2007 100: pp. 263-272.

L. T. Shenje, P. Andersen, M. K. Halushka, C. Lui, L. Fernandez, G. B. Collin, N. Amat-Alarcon, W. Meschino, E. Cutz, K. Chang, R. Yonescu, D. A. S. Batista, Y. Chen, S. Chelko, J. E. Crosson, J. Scheel, L. Vricella, B. D. Craig, B. A. Marosy, D. W. Mohr, K. N. Hetrick, J. M. Romm, L. F. Scott, D. Malle, J. K. Naggert, C. Kwon, K. F. Doheny, D. P. Judge, Mutations in Alstrom Protein Impair Terminal Differentiation of Cardiomyocytes, Nature Communications, Mar. 4, 2014, vol. 5, Article No. 3416.

Li H, Sun S, Liu H, Chen H, Rong X, Lou J, Yang Y, Yang Y, Liu H, Use of a biological reactor and platelet-rich plasma for the construction of tissue-engineered bone to repair articular cartilage defects, Exp. Ther. Med. Aug. 2016, vol. 12(2) pp. 711-719.

Masuda S, Shimizu T, Three-dimensional cardiac tissue fabrication based on cell sheet technology, Adv. Drug Deliv. Rev. Jan. 2016, vol. 96 pp. 103-109.

Ramachandran SD, Schirmer K, Munst B, Heinz S, Ghafoory S, Wolfl S, Simon-Keller K, Marxa Oie CI, Ebert MP, Walles H, Braspenning J, Breitkopf-Heinlein K, In Vitro Generation of Functional Liver Drganoid-Like Structures Using Adult Human Cells, PLoS One, Oct. 2015, vol. 10(10) pp. e0139345.

De Peppo GM, Vunjak-Novakovic G, Marolt D, Cultivation of human bone-like tissue from pluripotent stem cell-derived osteogenic progenitors in perfusion bioreactors, Methods Mol Biol. 2014 vol. 1202 pp. 173-184.

Bhumiratana S, Bernhard JC, Alfi DM, Yeager K, Eton RE, Bova J, Shah F, Gimble JM, Lopez MJ, Eisig SB, Vunjak-Novakovic G, Tissue-engineered autologous grafts for facial bone reconstruction, Sci. Transl. Med. Jun. 2016, vol. 8(343) pp. 343ra83.

Ding M, Henriksen SS, Wendt D, Overgaard S, An automated perfusion bioreactor for the streamlined production of engineered osteogenic grafts, J. Biomed. Mater. Res. B Appl. Biomate., Apr. 2016, vol. 104(3) pp. 532-537.

Figallo E, Cannizzaro C, Gerecht S, Burdick JA, Langer R, Elvassore N, Vunjak-Novakovic G, Micro-bioreactor array for controlling cellular environments, Lab Chip, Jun. 2007, vol. 7(6) pp. 710-719.

Hansmann J, Groeber F, Kahlig A, Kleinhans C, Walles H., Bioreactors in tissue engineering—principles, applications and commercial constraints. Biotechnol. J., Mar. 2013, 8(3) pp. 298-307.

Wang Z, Kim K., Organ-on-a-Chip Platforms for Drug Screening and Tissue Engineering, Biomedical Engineering: Frontier Research and Converging Technologies, Jan. 2016, pp. 209-233.

IPRP mailed Sep. 1, 2016 in Application No. PCT/US2016/031768.

Eschenhagen et al.: "Cardiac tissue engineering.", Transpl. Immunol., vol. 9, No. 2-4, May 2002 (May 1, 2002), pp. 315-321.

Masutani et al.: "Levosimendan restores the positive force-frequency relation in heart failure.", Am J Physiol Heart Circ Physiol., vol. 301, No. 2, Aug. 2011 (Aug. 1, 2011), pp. H488-H49.

Tulloch et al.: "Growth of engineered human myocardium with mechanical loading and vascular coculture.", Circulation Research., vol. 109, No. 1, 2011, pp. 47-59.

Yazawa et al.: "Using induced pluripotent stem cells to investigate cardiac phenotypes in Timothy syndrome.", Nature, vol. 471, No. 7337, Mar. 10, 2011 (Mar. 10, 2011), pp. 230-234.

Shamir and Ewald, "Three-dimensional organotypic culture: experimental models of mammalian biology and disease." Nat Rev Mal Cell Biol. Oct. 2014;15(10):647-64. doi: 10.1038/nrm3873. Epub Sep. 17, 2014. (Year: 2014).

Liau et al. "Pluripotent stem cell-derived cardiac tissue patch with advanced structure and function."Biomaterials. Dec. 2011;32(35):9180-7 (Year: 2011).

Ronaldson et al. "P-431: Human iPS Cell Based Cardiac Microtissue Platform for Predictive Toxicity Studies" Tissue Engineering Part A.Dec. 2014. Published in vol. 20 Issue S1: Dec. 3, 2014 (Year: 2014).

Stevens et al. "Physiological function and transplantation of scaffold-free and vascularized human cardiac muscle tissue."Proc Natl Acad Sci U SA. Sep. 29, 2009; 106(39): 16568-16573. (Year: 2009).

IPRP mailed Sep. 29, 2017 in Application No. PCT/US2017/041996.

Eliza Cimetta, Elisa Figallo, Christopher CANNI77ARO, Nicola Elvassore, and Gordana Vunjak-Novakovic, Microbioreactor arrays for controlling cellular environments: design principles for human embryonic stem cell applications Methods. Feb. 2009 ; 47(2): 81-89.

Meyvantsson I and Beebe DJ, Cell Culture Models in Microfluidic Systems, Annu. Rev. Anal. Chem. 2008, 1:423-49.

* cited by examiner

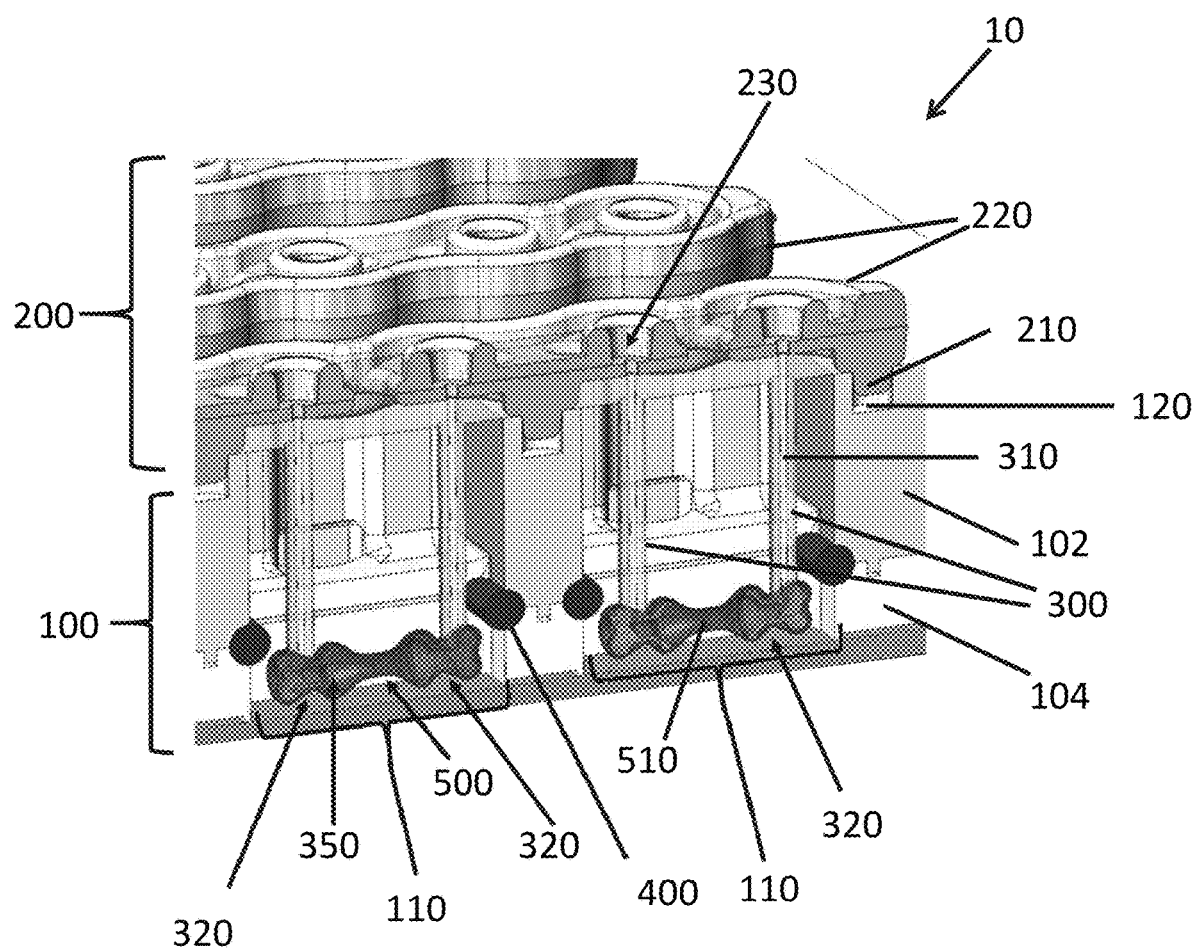

BIOREACTOR SYSTEM FOR ENGINEERING TISSUES

INCORPORATION BY REFERENCE

This application relates to International Publication No. WO 2016/183143 of International Application No. PCT/US2016/031768, filed May 11, 2016, which claims priority to U.S. Provisional Patent Application Ser. No. 62/159,953, filed May 11, 2015, 62/198,502, filed Jul. 29, 2015, and 62/275,385 filed Jan. 6, 2016, each of the contents are incorporated herein by reference in their entireties.

CROSS-REFERENCE TO RELATED APPLICATIONS

The present application is a continuation of International Application No. PCT/US2017/041996, filed on Jul. 13, 2017, which claims priority to U.S. Provisional Application No. 62/361,648, filed on Jul. 13, 2016 which is herein incorporated by reference in its entirety.

STATEMENT OF GOVERNMENT INTEREST

This invention was made with government support under EB017103 awarded by the National Institutes of Health. The government has certain rights in the invention.

TECHNICAL FIELD

The disclosed subject matter relates to a bioreactor for preparing engineered three-dimensional micro-sized tissue. The bioreactor platform is configurable and allows incorporation of multiple tissue types connected to each other by perfused microfluidic conduits established to recapitulate key interactions of interest for drug testing and modeling of disease.

BACKGROUND

Advances in the fields of stem cell biology and tissue engineering enable the manufacture of human, and more generally animal, tissues in vitro. These tissues can potentially be used as platforms for drug testing or for studies of physiology, e.g., cardiac and pathophysiology. In order to utilize engineered tissues for drug testing and other uses, the bioengineered tissue must be matured in vitro. For example, desired disease phenotypes must be induced.

Bioreactors are important in tissue engineering, and should provide reproducible production of tissue constructs. Typical bioreactors for multi-tissue in vitro culture utilize a two-dimensional approach, which may also include microfluidic channels for media exchange. The disclosed bioreactor enables the culture of more physiologically relevant micro tissues in three dimensions, provides a means to exchange tissue specific media for each tissue type, and enables micro-tissue circuits to be constructed with a common media that flows through an internal lumen within each micro-tissue.

SUMMARY

The disclosed subject matter provides a modular bioreactor configured to engineer mature, adult-phenotype, three dimensional microtissues, such as but not limited to iPS cell-based vascular, cardiac and tumor micro-tissues. The iPS based micro-tissues formed using the bioreactor are functional three dimensional tissue units having tissue-specific architectures ("ultrastructures") having an integrated vascular network, microfluidic endothelialized connections between tissue modules, which establish a functional representation of human biology in health, injury and disease.

In one embodiment, a bioreactor is provided for simultaneously providing multiple types of media to a tissue without mixing of the various media sources and to allow engineering of multiple tissues in a common reactor. The bioreactor comprises a modular body defining a first well for engineering a first tissue and a second well for engineering a second tissue. The bioreactor further comprises a first media inlet flow path in fluid communication with the first well, and a first media outlet flow path in fluid communication with the first well. A first tissue-specific media is able to be injected into the first well via the first media inlet flow path, and wherein the first tissue-specific media can exit the first well via the first media outlet flow path. The bioreactor further comprises a second media inlet flow path in fluid communication with the second well, and a second media outlet flow path in fluid communication with the second well. Accordingly, a second tissue-specific media is able to be injected into the second well via the second media inlet flow path, and the second tissue-specific media can exit the second well via the second media outlet flow path. The bioreactor further comprises a pair of first pillars. Each first pillar having an upper end and a lower end, wherein the upper end is engaged with a first support member of a lid insert such that each first pillar extends downwardly from the first support member along a longitudinal axis with the lower end of each first pillar being disposed in the first well. The pair of first pillars each comprise a central channel to permit fluid communication between the first pillars. Additionally, the pair of first pillars are capable of supporting the first tissue and providing a common media to an internal cavity of the first tissue via the central channel of the pillars. In doing so, the common media does not mix with the first tissue-specific media in the first well. The bioreactor further comprises a pair of second pillars. Each second pillar having an upper end and a lower end, wherein the upper end is engaged with a second support member associated with the lid insert and arranged such that each second pillar extends downwardly from the second support member along a longitudinal axis with the lower end of each second pillar being disposed in the second well. In the second pillar pair, the lower ends are joined by a horizontal segment having a central channel in fluid communication with a central channel of each of the second pillars. In order to communicate the second media to the second tissue, at least a portion of each second pillar or the horizontal segment is formed of a permeable membrane. The permeable membrane, for example, can have a permeability of three microns or less. It should be understood that the first and second tissues and first and second tissue-specific medias can be tissues of different origin. For example, the first tissue is cardiac and the second tissue is bone and the first and second tissue-specific medias are tailored for the respective tissue.

The pair of first pillars can be in fluid communication with the central channel of the pair of second pillars via a connecting flow conduit such that the common media can flow between the first and second tissues in the first and second wells, respectively. The distance between the pair of first pillars and the distance between the pair of second pillars is, for example, each from about 3 mm to about 8 mm, and preferably about 6 mm.

The bioreactor may further comprise electrically conductive material disposed on the lateral side of each of the pair of first pillars. For example, the electrically conductive material is a carbon rod. The electrically conductive material can be in electrical communication with an electrical stimulator.

In certain embodiments, the lower end of each first pillar comprises a head, wherein the head comprises a flared end extending perpendicularly from the longitudinal axis, wherein the flared end defines an opening in communication with the central channel of the first pillar, wherein the openings of the flared ends of the pair of first pillars face each other and are aligned vertically and horizontally, wherein the heads of each first pillar provide a support surface for the first tissue, and wherein the opening is in communication with the internal cavity of the first tissue. The flared end can have a circular cross-section. The head of the pillars may further comprises a lateral portion extending outwardly in the direction opposite the flared end, and wherein the lateral portion does not contain an opening.

The modular body may further comprise one or more additional first wells for engineering additional first tissues and one or more additional second wells for engineering additional second tissues, wherein the one or more additional first wells is in fluid communication with the first media inlet flow path and the first media outlet flow path, and wherein the one or more additional second wells is in fluid communication with the second media inlet flow path and the second media outlet flow path. It should be understood that the bioreactor of the present disclosure can handle many different tissues and several samples of each tissue simultaneously. For example, the bioreactor may comprise 48 wells or 96 wells.

In any other the above embodiments, the modular body further defines a third well for engineering a third tissue, a third media inlet port providing access to a third media inlet flow path, wherein the third media inlet flow path is in fluid communication with the third well, a third media outlet flow path in fluid communication with the third well, wherein a third tissue-specific media is able to be injected into the third media inlet port and directed to the third well via the third media inlet flow path, and wherein the third tissue-specific media can exit the third well via the third media outlet path. In this embodiment, a second pair of second pillars extends into the third well, wherein the central channel of the second pair of second pillars is in communication with the central channel of the pair of first pillars and central channel of the pair of second pillars via a connecting flow conduit such that the common media can flow between the first, second, and third tissues in the first, second, and third wells, respectively.

In another aspect, a bioreactor is provided for common media exchange across multiple tissue types via vascularized channels. In this embodiment, the modular body is similar to that described above for providing tissue-specific media for the wells. However, in this embodiment, the bioreactor comprises a membrane filter layer disposed below the modular body, and a second layer disposed below the membrane filter layer. Here, the second layer comprises at least one channel and is positioned such that the channel is disposed underneath the first and second well. The channel is therefore in fluid communication with the first and second wells via the membrane filter layer. The membrane filter layer prevents cell migration between the layer and the first and second wells.

In one embodiment, the bioreactor further comprises an inlet port positioned at one end of the channel and an outlet port positioned on the opposite end of the channel, and wherein the inlet and outlet ports are accessible through fluid conduits disposed through the modular body.

It should be understood that the modular body may further comprise one or more additional first wells for engineering additional first tissues and one or more additional second wells for engineering additional second tissues. It should also be understood that the bioreactor may comprise multiple channels and arranged such that a single channel may be in fluid communication with multiple wells supporting different tissues or the same tissue.

BRIEF DESCRIPTION OF THE DRAWINGS

FIG. 1 provides a perspective cross-section of one embodiment of a well configuration for use with cardiac tissue in a bioreactor of the present disclosure.

Figure 2A:
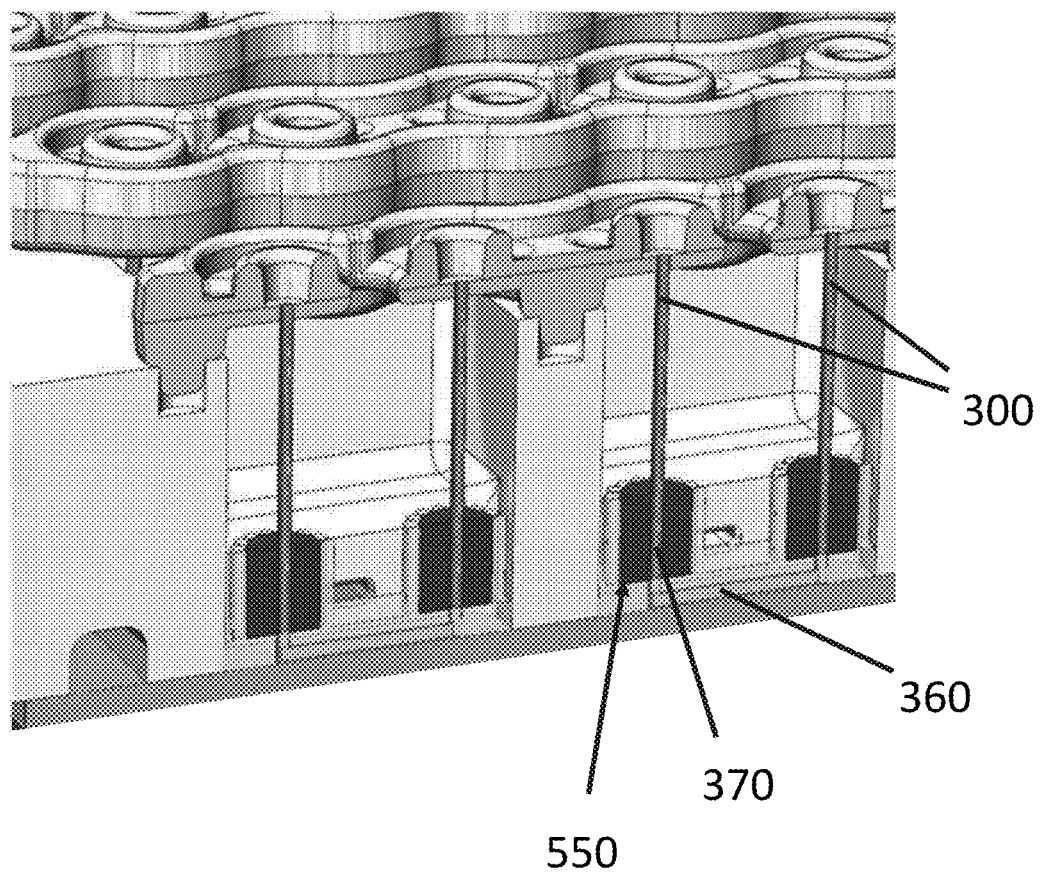
FIG. 2A provides a perspective cross-section of one embodiment of a well configuration for use with liver tissue in a bioreactor of the present disclosure.

While the present disclosure is susceptible to various modifications and alternative forms, specific example instances have been shown in the figures and are herein described in more detail. It should be understood, however, that the description of specific example instances is not intended to limit the invention to the particular forms disclosed, but on the contrary, this disclosure is to cover all modifications and equivalents as illustrated, in part, by the appended claims.

DETAILED DESCRIPTION OF EXEMPLARY EMBODIMENTS

Generally, the described subject matter provides a bioreactor system for engineering 3-D human tissue. The bioreactor system is useful in carrying out methods to form and mature engineered micro-tissue. The engineered adult-like micro-tissue is suitable for personalized screening and disease modeling as described in PCT/US2016/031768, which is incorporated herein in its entirety. Accordingly, the bioreactor system described herein is useful for methods of engineering, three-dimensional, functional, adult-like micro-tissue. The micro-tissue described includes heart, vascular and tumor tissues. However, the bioreactor system taught may be extrapolated to other tissues.

The bioreactor platform contains an array of modular tissue specific media reservoirs, and may take the patterning of a standard multi-well plate for convenience (e.g. 24 well, 48 well, 96 well). For each reservoir within the array, two ports are located at the top of the manifold and provide a fluidic path into the reservoir for media exchange. In one module, the configuration of the reservoir allows force measurements from the deflection of the elastic pillars and can be configured to bioengineer heart or skin tissues. A separate module can support bioengineered tissues formed from cellular aggregates, e.g. liver, and also tissues formed onto rigid scaffolds, e.g. bone. This second configuration incorporates a perfuseable lumen formed from a permeable membrane that can pass through the micro tissue. In one aspect the modular bioreactor comprises a tissue specific media reservoir comprising a top manifold and a bottom manifold, each adapted to form an interlocking relationship. A lid insert capable of latching on to the top manifold is disposed on the top surface of the top manifold. The lid insert further includes a plurality of holes, each hole configured to receive a pillar body. The lid is comprised of a rigid plastic component and overmolded with an elastomeric component to allow for the incorporations of deformable pillars. The rigid plastic facilitates handling by the user, aligns the pillars into a repeatable location, provides ports for fluidic connections, and interlocking geometry for installing the lid onto the reservoir manifold. The lid may further include apertures disposed between adjacent holes to facilitate attachment of the elastomer to the plastic and provide robust anchoring of the pillar bodies. The pillar includes an elongate body between proximal and distal ends. The elongate body may be tubular (having a central channel) or solid. The pillar includes a head disposed at the distal end of the elongate body of the pillar. In some embodiment, the bioreactor includes an electrical stimulator, e.g. carbon electrodes.

Referring to FIG. 1, one embodiment of the bioreactor system is depicted. Generally, the bioreactor system 10 includes a modular body defining a tissue specific media reservoir platform 100. The tissue specific media reservoir platform 100 comprises a manifold top layer 102 interlocking a manifold bottom layer 104 defining a plurality of enclosed wells 110. A lid insert 200 comprising one or more support members 220 is removably engaged to the top surface of the tissue specific media reservoir platform 100 via a recess 120 of a size sufficient to receive a downward projection 210 extending from support member 220. A pair of pillars 300 extends downwardly from support member 220 into well 110. In one embodiment, the distance between pillars 300 in each well is from about 3 mm to about 8 mm, and more preferably about 6 mm. It should be understood however that the distance between pillars 300 may vary based on the particular need for the tissue being supported.

Figure 3A:
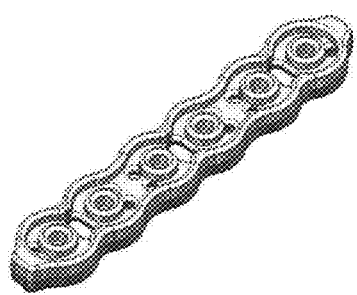
FIG. 3A provides a perspective view of one embodiment of a support member for use with cardiac tissue in a bioreactor of the present disclosure.
Figure 3B:
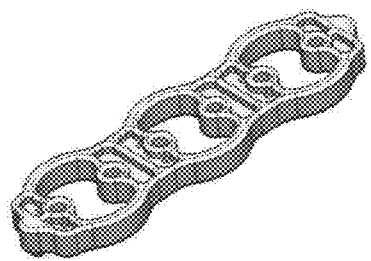
FIG. 3B provides a perspective view of one embodiment of a support member for use with skin tissue in a bioreactor of the present disclosure.
Figure 3C:
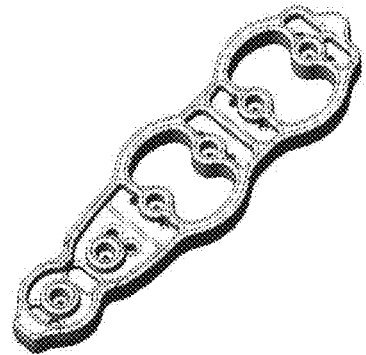
FIG. 3C provides a perspective view of one embodiment of a support member for use with both a cardiac tissue and skin tissue in a bioreactor of the present disclosure.
Figure 3D:
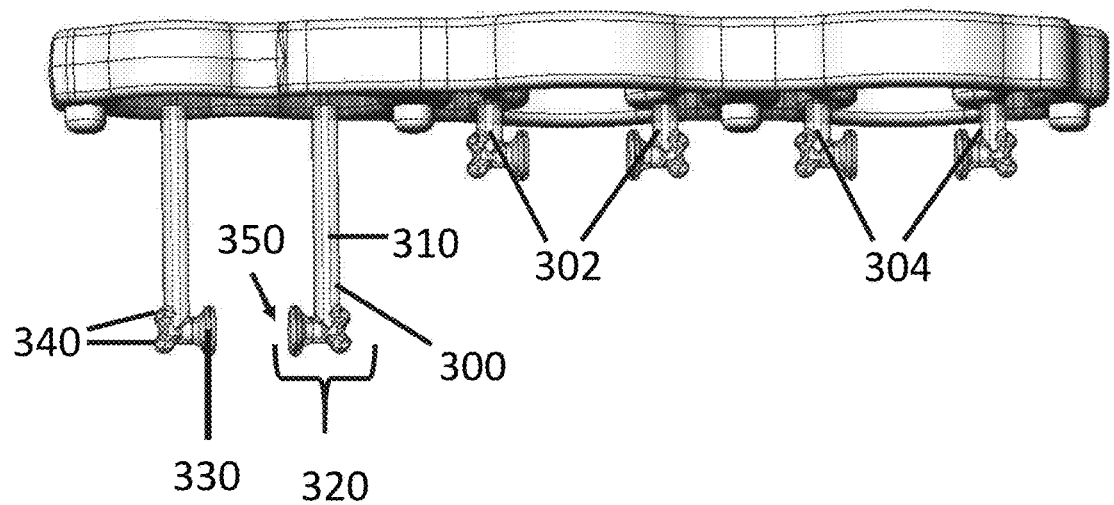
FIG. 3D is a side view of the support member depicted in FIG. 3C and further depicting various pillar designs used to support cardiac tissue and skin tissue in a bioreactor of the present disclosure.

As shown in FIG. 1 and FIG. 3D, the pillars 300, in one embodiment, terminate at their lower end with a head 320. In this embodiment, the pillar head 320 is configured for engineering tissues having a lumen or internal cavity, such as cardiac tissue. The heads 320 of pillars 300 are therefore aligned vertically and horizontally within the well 110 to provide a support surface for the tissue 500 extending between the heads 320 of the pair of pillars 300. Referring now to FIG. 3D, in one embodiment, each head 320 comprises a flared end 330 extending perpendicularly from the longitudinal axis of pillar 300. The flare at the pillar head facilitates tissue attachment by increasing surface area. Flared end 330 defines an opening 350 which is in fluid communication with a central channel 310 that runs internally along the longitudinal axis of pillar 300. Referring now to FIG. 1, openings 350 face each other such that a flow path is defined through an internal cavity or lumen 510 of tissue 500. In this way, a common media can be circulated through central channel 310 of one of the pillars 300, innervate the tissue 500 via the internal cavity 510 and exit via the central channel 310 of the opposing pillar 300. As shown in FIG. 3D, head 320 may further comprise one or more lateral portions 340 extending outwardly in the direction opposite the flared end 330. The lateral portion 340 is solid such that it does not contain an opening and is to facilitate tissue attachment to the head 320.

The central channel within the pillar allows for a second media type to be delivered within the micro tissue. For example, a cardiac micro tissue is supported by cardiac-specific media surrounding the tissue in the well, while a second media type to support vascular tissue can perfuse through the internal channel of the micro-tissue. The hollow pillars provide access to the internal lumen within the tissue and isolate the two media types from mixing. The 3-D cardiac tissue formed accurately creates tissue having mature adult-like phenotype. Thus, it can be used for assays such as strain mapping, force analysis, and voltage mapping to measure a drug's impact on function at the tissue level, for example, cardiac function at a tissue level.

Furthermore, the central channel 310 of adjacent wells can be connected to permit the common media to flow through multiple wells as shown in FIG. 8B. Support members 220 provide access points 230 to the central channels 310 of the pillars 300.

The bioreactor system is capable of simultaneously applying mechanical and electrical field stimulation to the tissue introduced to the system. To facilitate electrical stimulation, a plurality of rods 400 are disposed between the top and bottom interlocking manifolds and transverse the medial reservoir platform 100. The carbon rods enable electrical stimulation of the micro tissue. They may be electrically connected to a stimulator to control voltage, current, and the profile of the stimulation waveform.

Figure 2B:
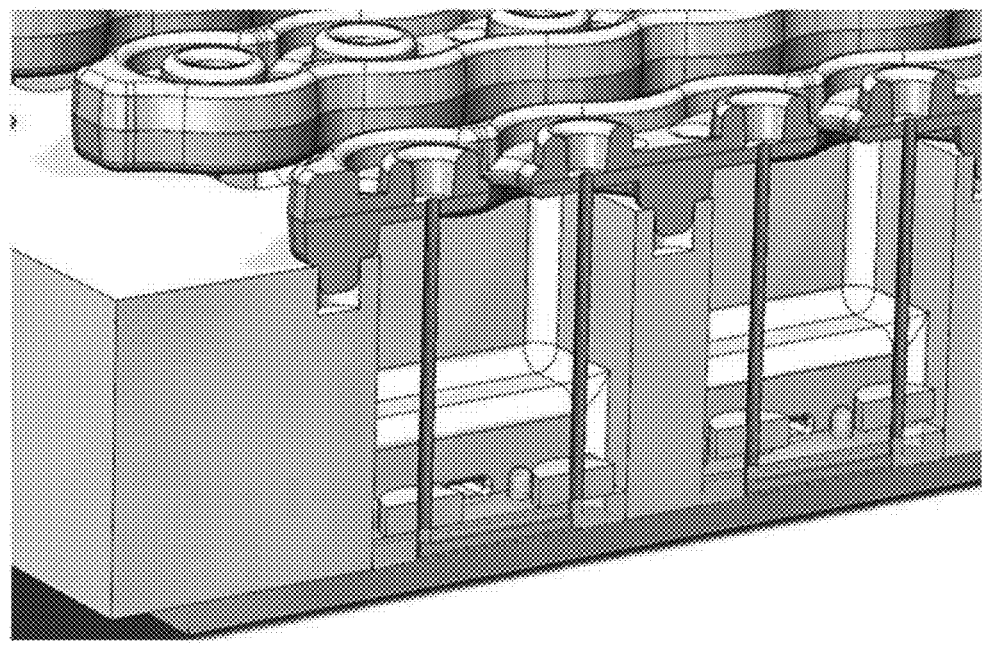
FIG. 2B provides a perspective cross-section of one embodiment of a well configuration for use with bone tissue in a bioreactor of the present disclosure.

In one aspect, the subject matter provides a modular bioreactor confirmed for engineering various tissues. As discussed above, FIG. 1 provides a design for use with cardiac tissue. Referring now to FIG. 2A, a pillar configuration is depicted for supporting liver tissue 550. In this embodiment, each pair of pillars 300 may be connected by a horizontal segment 360. The horizontal segment 360 also comprises a central channel (not shown) that is in fluid communication with the central channels (not shown) of the pair of pillars 300. In this embodiment, a portion 370 of the pillar 300 in contact with the liver tissue is formed of a permeable membrane to provide fluid access to the tissue from a common media running through the pillars 300. Alternatively, the entire pillar 300 may be formed of a permeable membrane. For example, but not limitation, the permeable membrane consists of dialysis tubing. Permeability of the order of 1 micron and smaller pore size is acceptable. The membrane may be formed from materials such as dialysis tubing, expanded PTFE, or a variety of electrospun polymers. Liver tissue 550 may also be supported by horizontal segment 350 (not shown). FIG. 2B provides a similar design as that in FIG. 2A for use with bone or bone tumor tissue.

Figure 2C:
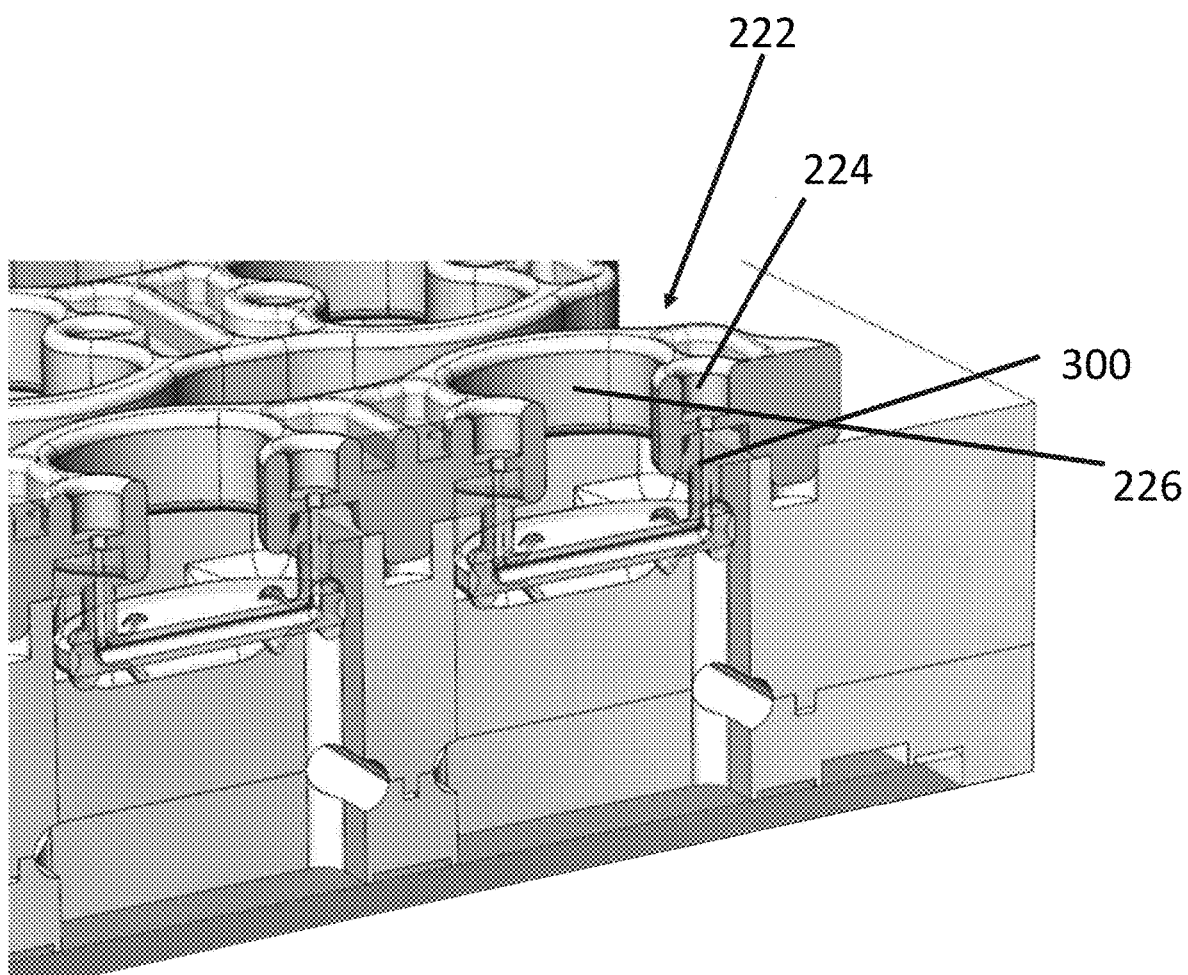
FIG. 2C provides a perspective cross-section of one embodiment of a well configuration for use with skin tissue in a bioreactor of the present disclosure.

Referring now to FIG. 2C, a bioreactor designed for engineering skin tissue is provided. Support member 222 has a plurality of circular holes 224 configured to hold the pillar body 300 and spaced apart by a spacing aperture 226. Support member includes a longitudinal body having opposing sides and a top and bottom surface having a width therebetween. The opposing sides have a sinusoidal shape along the perimeter of the insert. The top and bottom surfaces define a plurality of substantially circular holes and apertures defined by circumferentially opposing arms defined by the sides of the insert. In this example for skin, support member 222 forms an open aperture 226 above the tissue reservoir to facilitate access to the chamber from above for user interaction, or to facilitate microscopic imaging.

FIGS. 3A-3C depict various types of support members. Referring to FIG. 3C, a support member is configured for a bioreactor that is capable of engineering different types of tissues in the same tissue specific reservoir platform. In this embodiment, the support member has a first section for accommodating two skin tissue reservoirs and a second section for accommodating a cardiac tissue reservoir. The first section comprises first and second circular holes defined through the top and bottom solid surfaces of the insert. The second section comprises a plurality of circular holes and first and second spacing apertures therebetween. FIG. 3A depicts a support member for three adjacent reservoirs of cardiac tissue, and FIG. 3B depicts a support member for accommodating three adjacent reservoirs of skin tissue.

FIG. 3D provides a side view of the support member depicted in FIG. 3C. The first pair of pillars 300 is designed to engineer cardiac tissue as described above in more detail and in FIG. 1. The second pair of pillars 302 and third pairs of pillars 304 are designed to facilitate skin tissue. In one embodiment, the pillars 302, 304 comprise a central channel thereby providing fluid access to an internal lumen throughout the tissue. Pillars 302, 304 are shorter to facilitate a higher tissue location within the media reservoir. In particular for skin, this higher configuration provides an air-liquid interface which is desired.

Figure 4A:
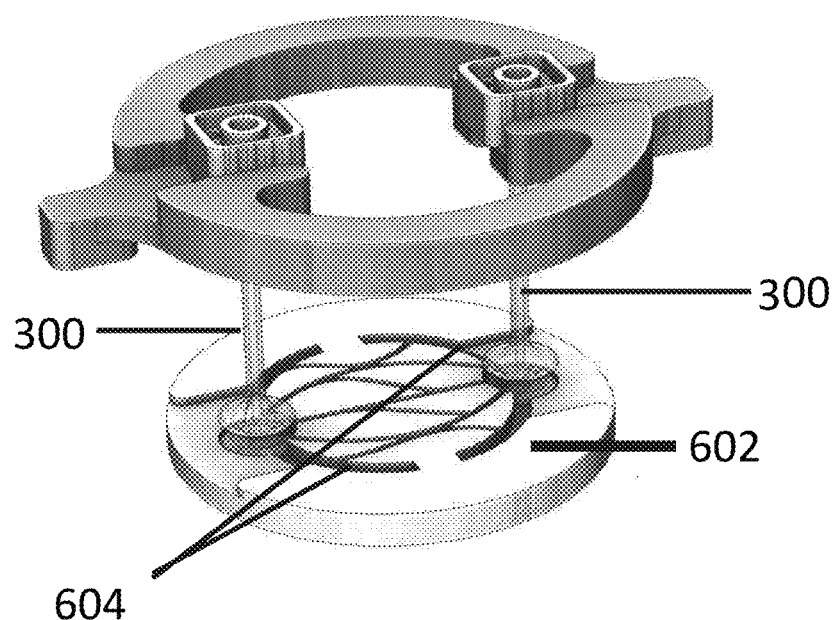
FIG. 4A is a perspective view of an isolated well configuration for use with skin tissue in a bioreactor of the present disclosure.
Figure 4B:
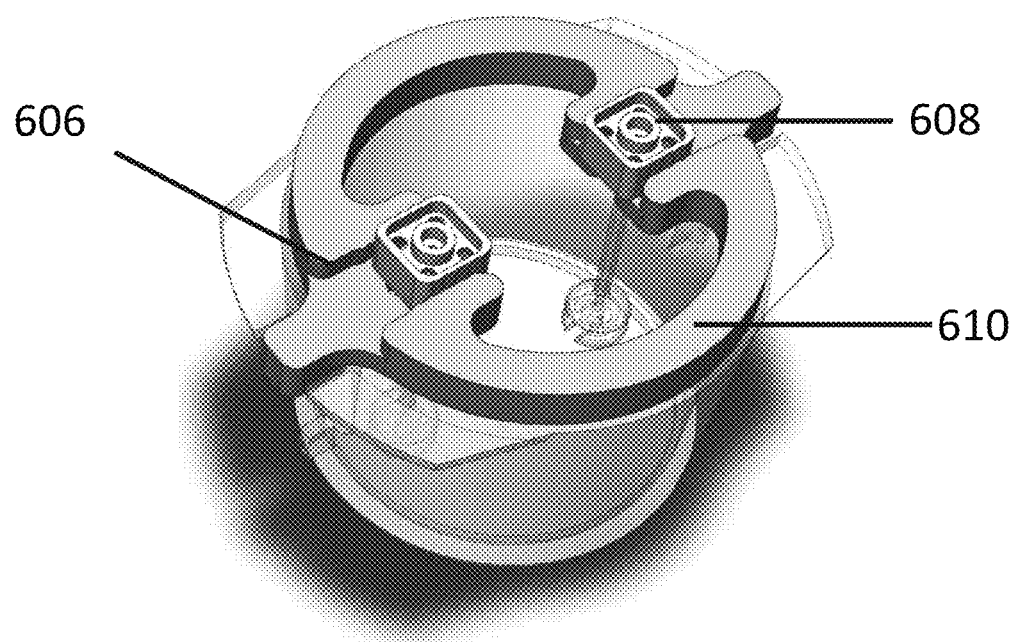
FIG. 4B is a top view of an isolated well configuration for use with skin tissue in a bioreactor of the present disclosure.
Figure 4C:
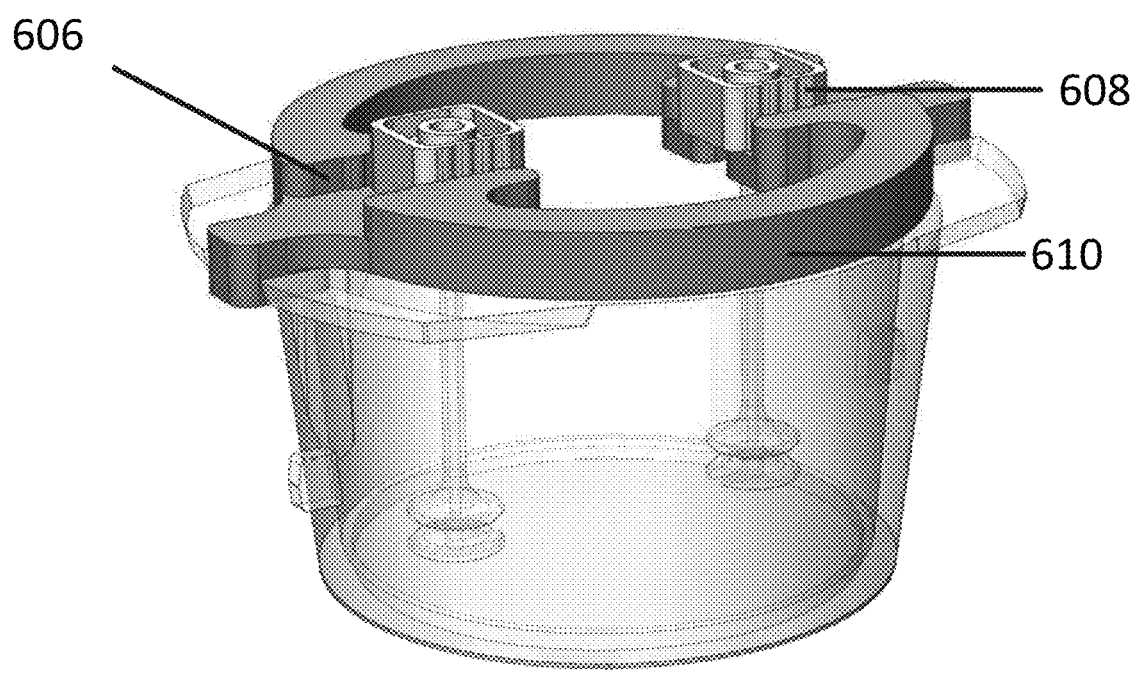
FIG. 4C is a side view of the isolated well configuration depicted in FIG. 4B.

In another embodiment, a bioreactor for formation of skin tissue is provided. Referring to FIG. 4A, pillars 300 are seated into a mold 602 for casting an agarose sacrificial network 604. The pillars are secured into a suspension structure. Referring now to FIG. 4B, the distance between first and second pillars can be incrementally adjusted by serrated groves 606 in the lid of the transwell. In this manner, the pillar proximal end includes a polygonal shaped cap 608 configured to be received into a serrated groove 606 in the lid 610. FIG. 4C depicts a side view of the bioreactor transwell configuration.

Figure 5A:
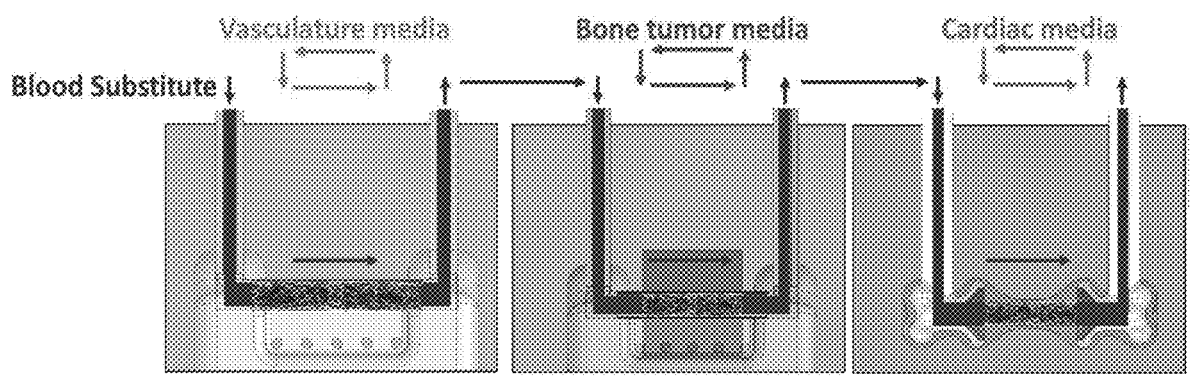
FIG. 5A depicts the flow path for a common media (blood substitute) between wells supporting various tissues.
Figure 5B:
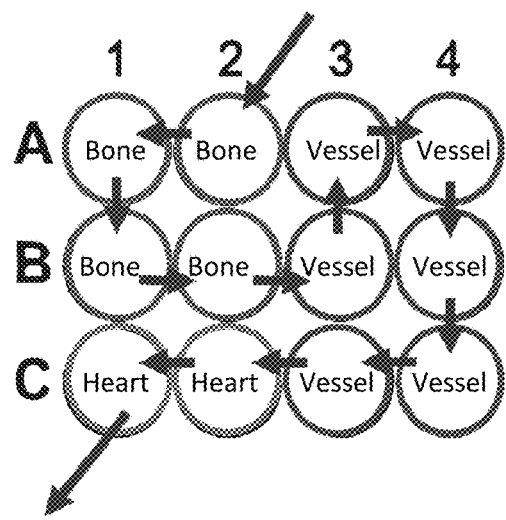
FIG. 5B provides an exemplary tissue distribution of a 12 well bioreactor with the arrows depicting the flow path of common media between the wells.
Figure 5C:
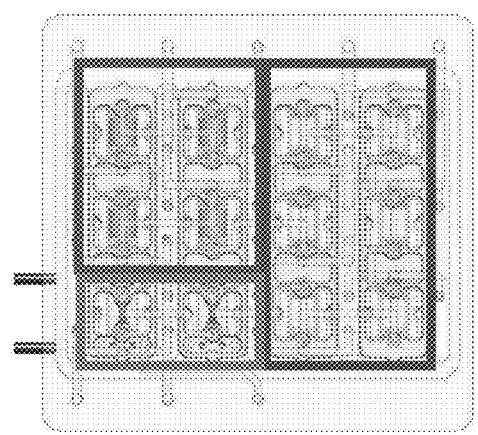
FIG. 5C provides a top cross-sectional view of a bioreactor configuration showing the tissue distribution described in FIG. 5B.
Figure 5D:
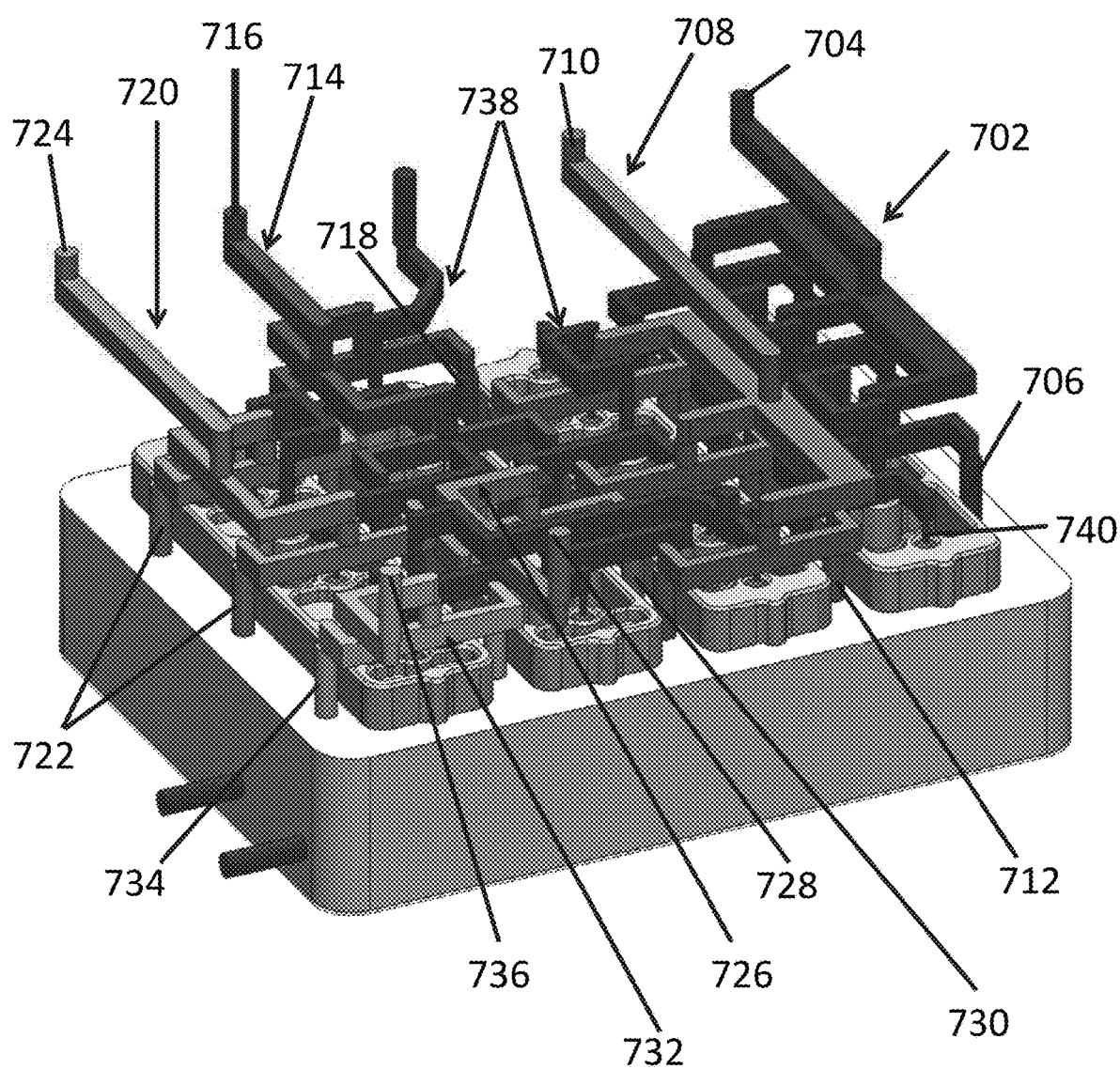
FIG. 5D is a perspective view of the modular body of a bioreactor of the present disclosure demonstrating both the various tissue-specific flow paths and the common media flow path.

A bioreactor for providing multiple media sources, for example, common blood surrogate perfusion and tissue-specific media, to various tissues is depicted in FIGS. 5A to 5C. The bioreactor is adapted to mimic in vivo physiology, and incorporate functional vasculature and maintain a tissue niche. In this regard, within each well there is both an inlet and an outlet to facilitate automated tissue-specific media exchanges. As shown in FIG. 5A, a blood substitute is introduced and travels or traverses first, second and third wells via the central channels of the first pillar to the horizontal segment supporting the tissue or the lumen of the cardiac tissue, and then exiting the opposite pillar via its central channel. Each well also contains tissue-specific media such as vasculature media (left well), bone tumor media (middle well), and cardiac media (right well). Thus, if desired, the blood surrogate can be prevented from mixing with the tissue specific media. In this regard, the bioreactor platform, as shown from a top view of the bioreactor in FIG. 5B, may have designated sections for engineering different tissues, such as bone (wells A1, A2, B1, and B2), cardiac tissue (wells C1 and C2) and vascular tissue (wells A3, A4, B3, B4, C3, C4). FIG. 5C illustrates the flow paths of distinct media types throughout the system. In this case, a first inlet flow path 702 provides, for example, incoming vasculature media that flows from a first inlet injection port 704 and is subsequently distributed to multiple wells via a series of first inlet well conduits 706 that terminate in the wells holding vascular tissue. A first outlet flow path 708 is in fluid communication with the same wells via a series of first outlet well conduits 710 which are in communication with the wells and routed to a common first outlet port 712. Similarly, a second inlet flow path 714 provides bone-specific media the flows from a second inlet injection port 716 and is subsequently distributed to multiple wells via a series of second inlet well conduits 718 that terminate in the wells holding bone tissue. A second outlet flow path 720 is in fluid communication with the same wells via a series of second outlet well conduits 722 which are in communication with the wells and routed to a common second outlet port 724. A third inlet flow path 726 provides cardiac-specific media the flows from a third inlet injection port 728 and is subsequently distributed to multiple wells via a series of third inlet well conduits 730 that terminate in the wells holding bone tissue. A third outlet flow path 732 is in fluid communication with the same wells via a series of third outlet well conduits 734 which are in communication with the wells and routed to a common third outlet port 736. Finally, a common media flow path 738 provides a common media, for example, a blood substitute, to each well via flow conduits 740 that are in fluid communication with the central channels of the pillars. As described above with respect to FIG. 5A, the common media is routed into and out from individual microtissue lumens, thus forming a multi-tissue fluidic perfusion circuit.

Figure 6A:
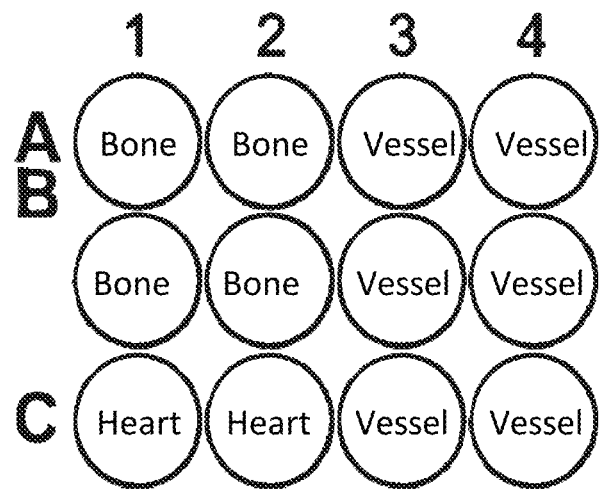
FIG. 6A provides an exemplary tissue distribution of a 12 well bioreactor.
Figure 6B:
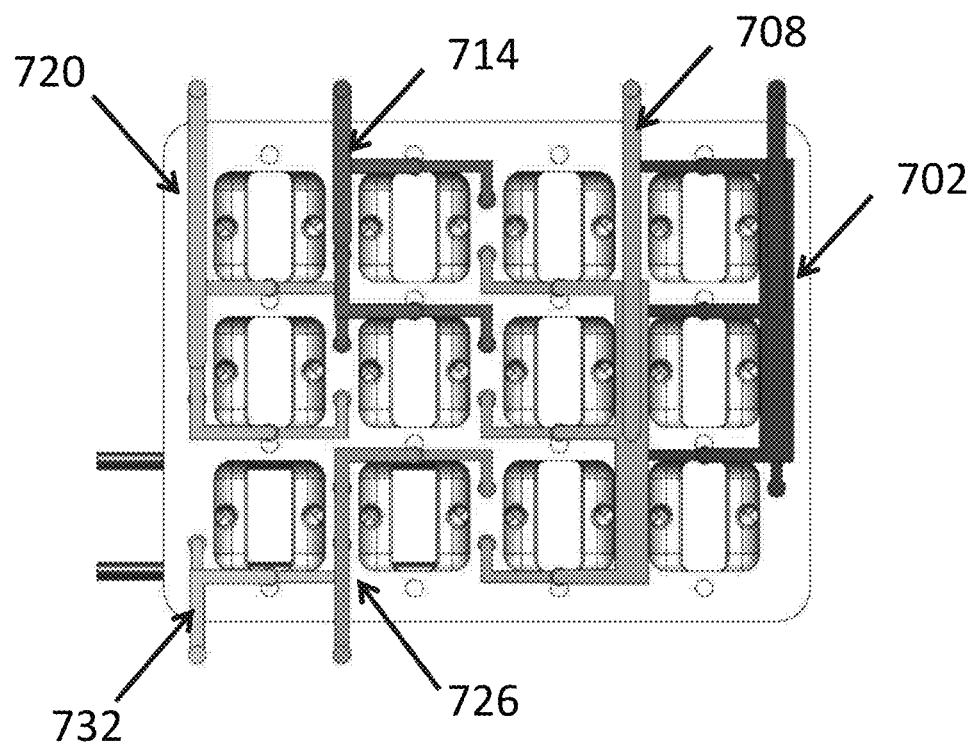
FIG. 6B is a top view of a bioreactor configuration incorporating the tissue distribution described in FIG. 6A and the tissue-specific flow paths for each tissue type.
Figure 6C:
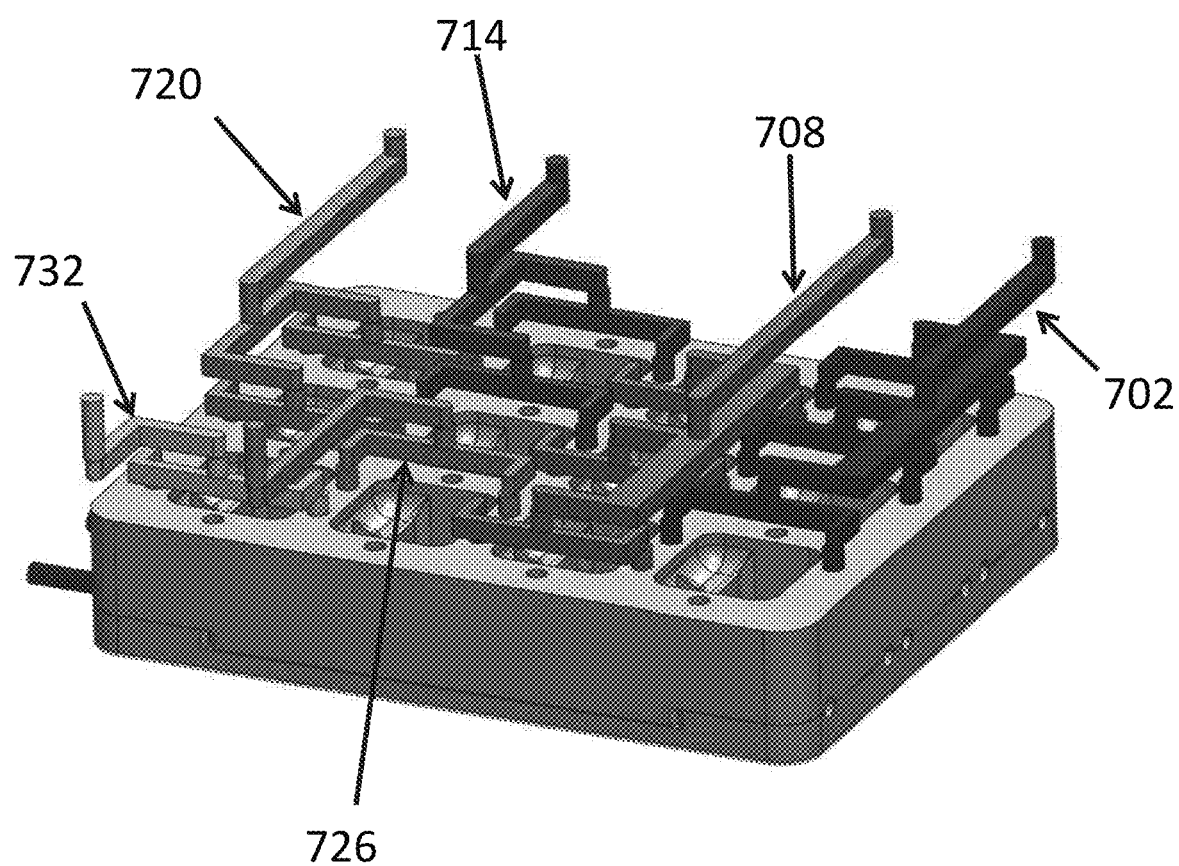
FIG. 6C is a perspective view of the bioreactor configuration depicted in FIG. 6B.
Figure 7A:
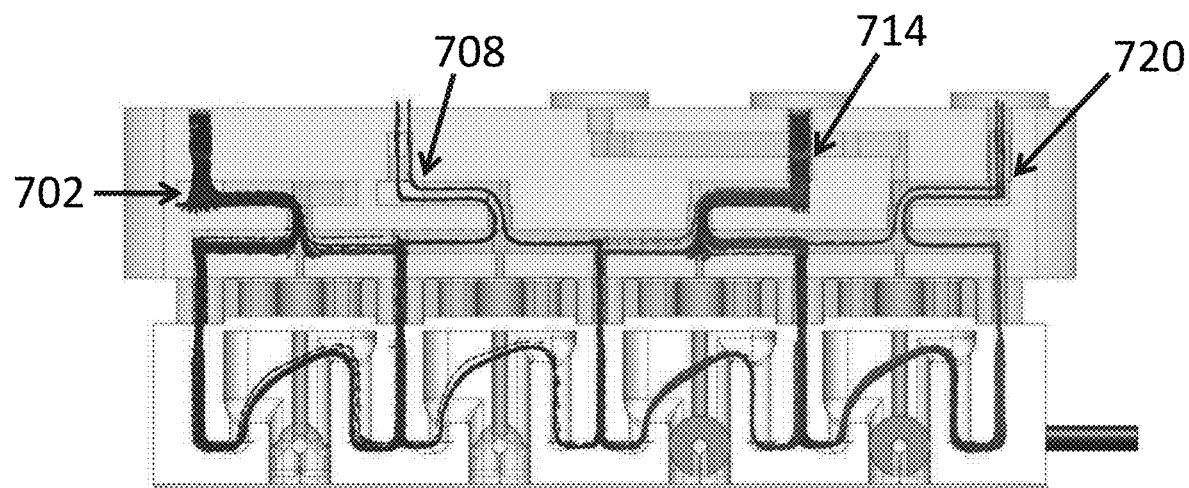
FIG. 7A is a side cross-sectional view of the bioreactor configuration depicted in FIG. 6B showing the flow path and velocity for the tissue-specific media innervating bone and vascular tissue.
Figure 7B:
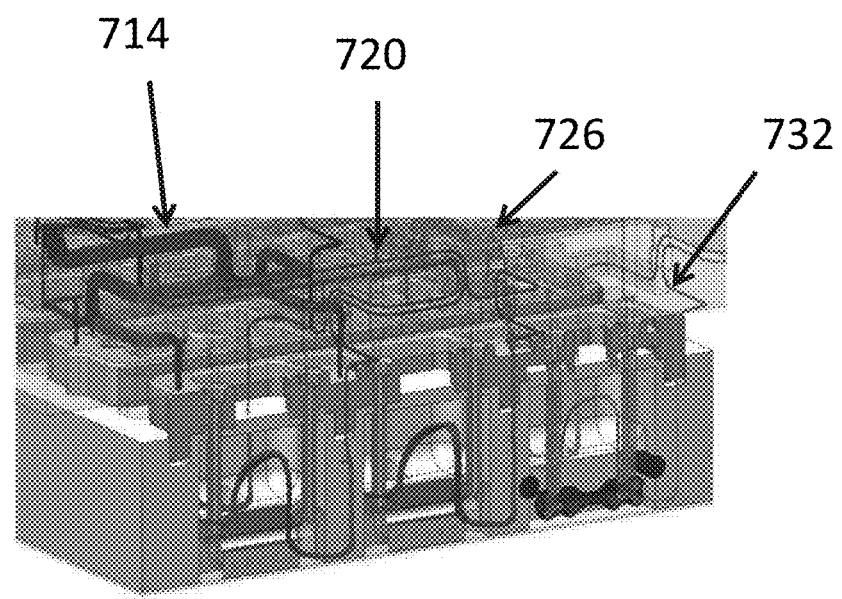
FIG. 7B is a perspective cross-sectional view of the bioreactor configuration depicted in FIG. 6B showing the flow path and velocity for the tissue-specific media innervating bone and cardiac tissue.
Figure 7C:
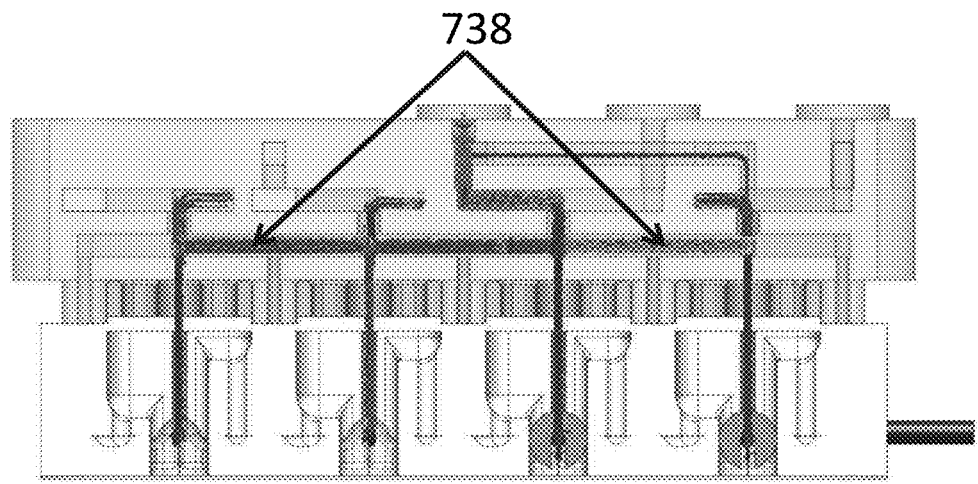
FIG. 7C is a side cross-sectional view of a bioreactor configuration showing the flow path and velocity for the common media innervating bone and vascular tissue.
Figure 7D:
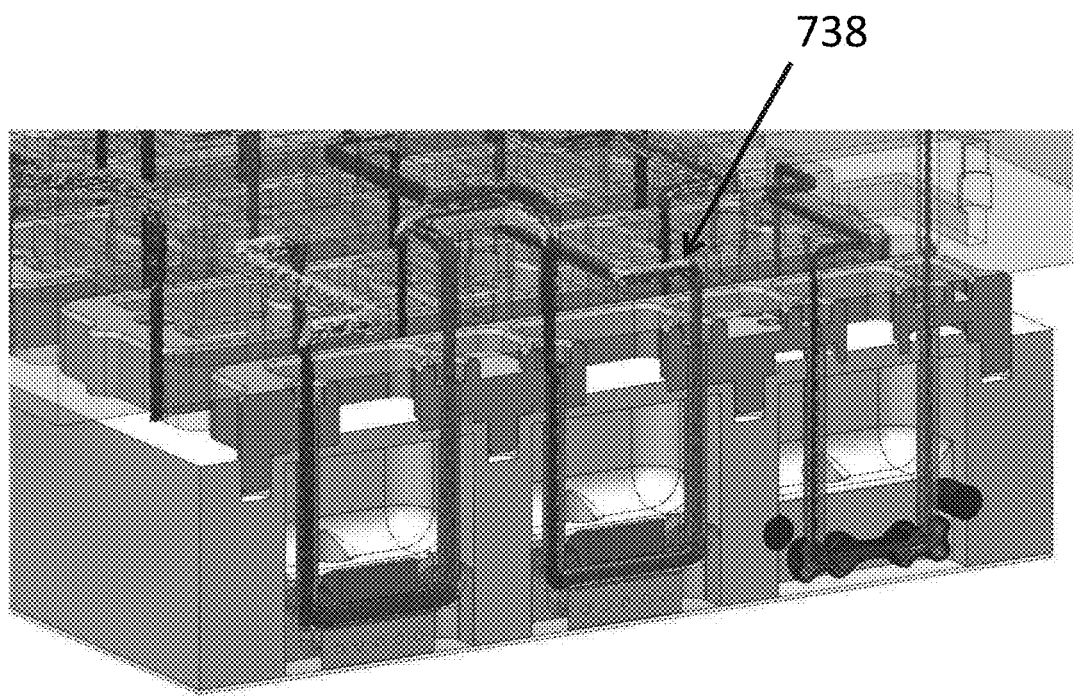
FIG. 7D is a perspective cross-sectional view of a bioreactor configuration showing the flow path and velocity for the common media innervating bone and cardiac tissue.
Figure 7E:
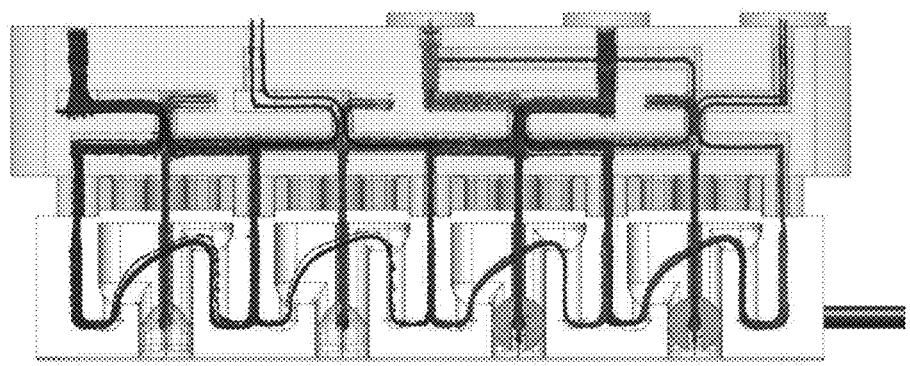
FIG. 7E is a cross-sectional view of the bioreactor configuration depicted in FIG. 6B showing both the flow path and velocity for the tissue-specific media and the common media innervating bone and vascular tissue.
Figure 7F:
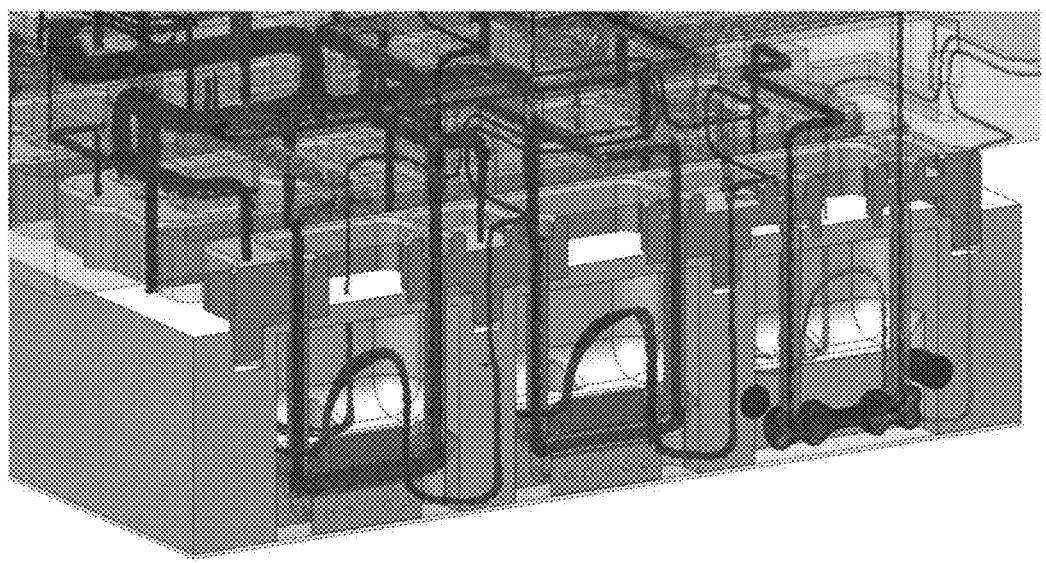
FIG. 7F is a perspective cross-sectional view of the bioreactor configuration depicted in FIG. 6B showing both the flow path and velocity for the tissue-specific media and the common media innervating bone and cardiac tissue.

Referring now to FIGS. 6A to 6C, a bioreactor designed for tissue specific media exchange for three separate tissue types is shown. In this embodiment, tissue specific media is provided for cardiac, bone, and vasculature tissues arranged in the wells as shown in FIG. 6A. FIG. 6B shows a top view of the reactor with the tissue-specific flow inlet paths and flow outlet paths. Specifically, a first, second, and third inlet flow path 702, 714, 726 provides vascular media, bone media, and cardiac media, respectively, to the wells holding the respective tissue via the series of conduits as described above in FIG. 5C. A first, second, and third outlet flow path 708, 720, 732 provides an outlet path for the tissue specific media as described above. A perspective view of this embodiment of the bioreactor is shown in FIG. 6C. FIGS. 7A, 7C, 7E show cross-sectional side views of the bioreactors highlighting the flow patterns (velocity) of tissue-specific media flow paths, common media flow paths, and fully integrated flow paths, respectively, as described above in FIGS. 5C, 6B, and 6C. FIGS. 7B, 7D, 7F show cross-sectional perspective view of the flow path configurations of FIGS. 7A, 7C, 7E, respectively. There are multiple types of media flowing through this system which are isolated from each other. The fluidic path of media exchange for all cardiac tissue wells, for example, is isolated from the fluidic path of media exchange for all bone tissue wells. The platform will incorporate one inlet and one outlet for each distinct tissue type, and an additional inlet and outlet to provide access to the common media/blood substitute.

Thus, the platform may be designed with a multi-well plate incorporating a flow distribution manifold to deliver media to multiple wells from a single port, and to drain media from multiple wells into a separate single port. The tubular posts are hollow and provide a passageway for the flow of a common media (a blood substitute, mimicking the role of blood connecting organs in our body) through the bioreactor. The bioreactor may be scaled-up to include, for example, 48 or 96 wells for development of the micro-tissue for scaled up screens.

Figure 8:
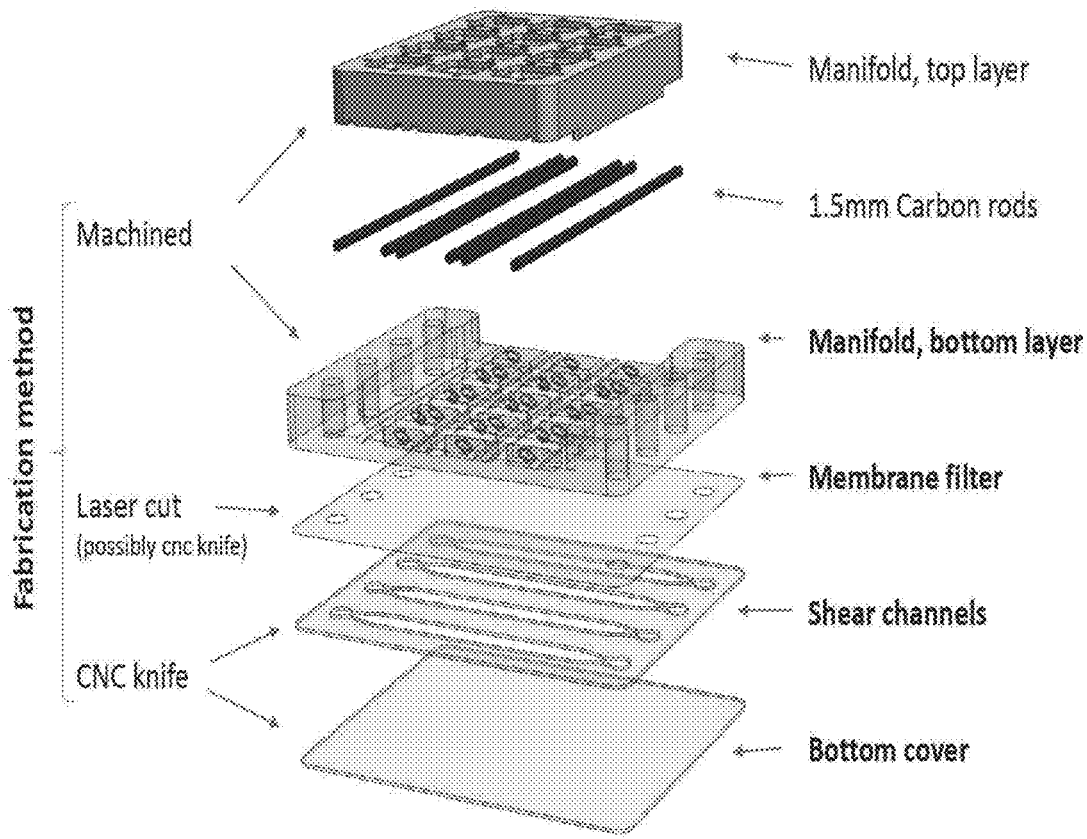
FIG. 8 is an exploded view of an alternative embodiment of a bioreactor of the present disclosure.
Figure 9:
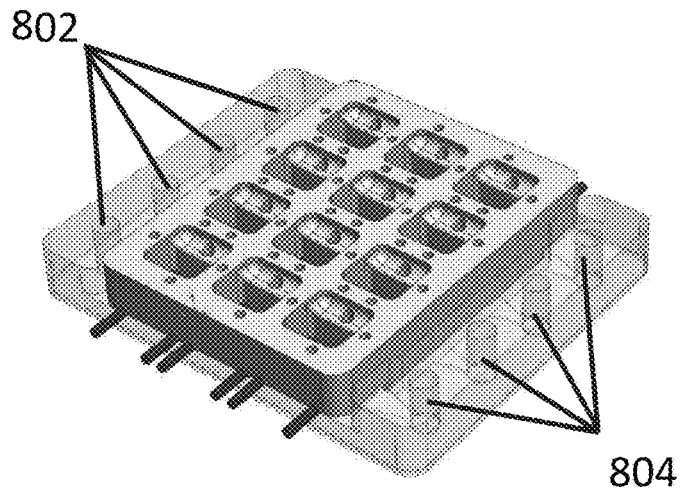
FIG. 9 is a perspective view of the constructed bioreactor shown in FIG. 8.

In another aspect of the present bioreactor, an alternative approach to culturing tissues utilizing a combination of tissue specific and common media is provided. Referring to FIGS. 8 and 9, the top manifold layer provides the tissue specific media as previously described above with electrically conductive material, such as carbon rods, disposed between the top manifold layer and bottom manifold layer. A membrane filter is disposed on the bottom surface of the bottom manifold and a layer to geometrically define fluidic channels is disposed between the membrane filter and the bottom cover. The common media is provided to the wells via the channels instead of through the pillars as previously described. The channels can be of a width and length to accommodate the wells in the top manifold layer. For example, the channels can have a width from about 3 mm to about 8 mm and preferably about 5 mm, and a length of about 8 mm to about 12 mm, and more preferably about 10 mm. The In this bioreactor configuration, multiple tissue types may be cultured within the reservoir located above the membrane filter layer, while vascular tissue lines the other side of the membrane filter. The filter is sized so as to prevent cell migration, but allow for cellular communication between vascular tissue and the micro tissue located on the other side of the membrane in the wells.

Figure 10:
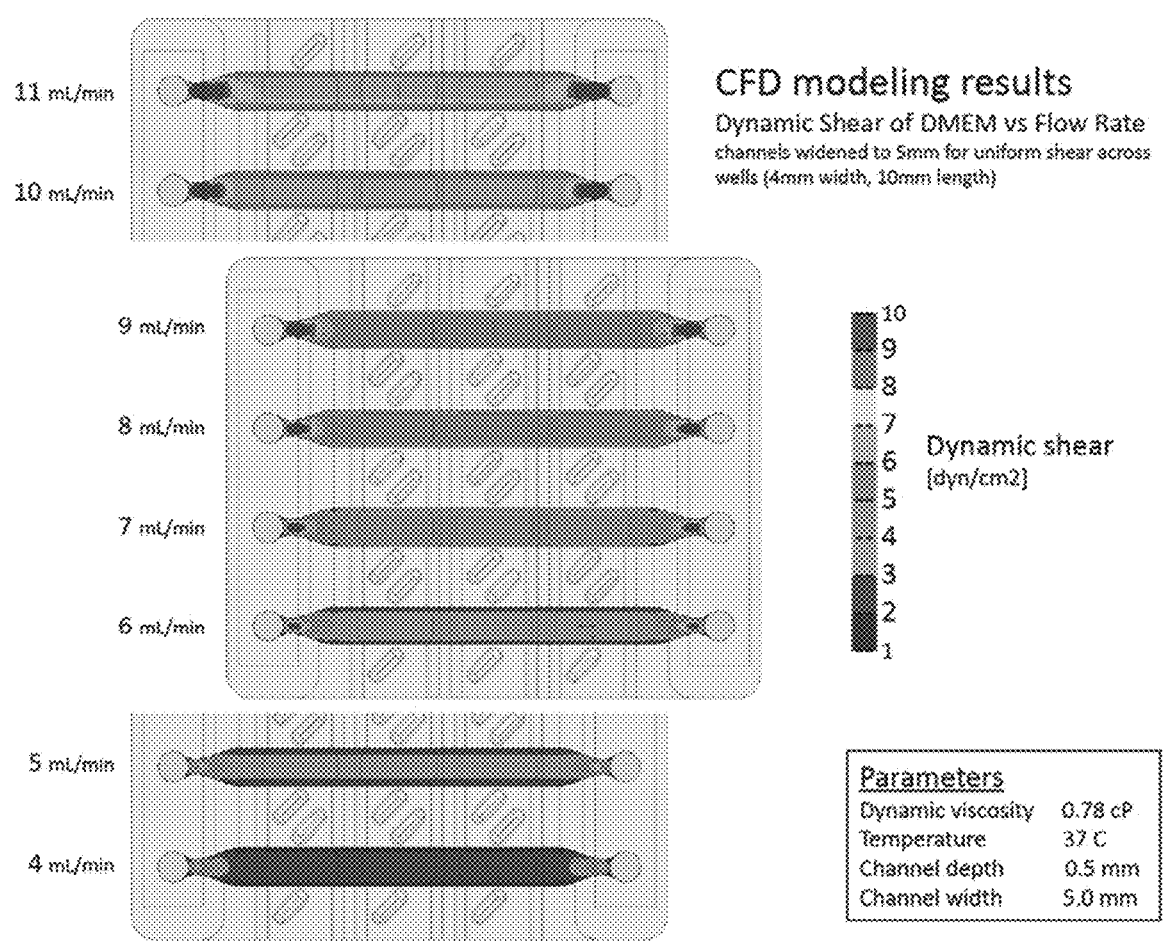
FIG. 10 depicts the dynamic shear of common media as it flows through the channels of the bioreactor of FIG. 9 at various flow rates.

FIG. 10 provides computational fluid dynamic modeling shows how one may adjust the volumetric flow rate of vascular media to achieve optimal dynamic shear values under the following parameters: channel width of 5 mm; channel depth of 0.5 mm; dynamic velocity of 0.78 cP; and temperature of 37° C.

The bioreactor platform is suitable for assembly and perfusion of micro-tissues formed from iPS C2a and for iPS hepatocytes and other iPS cells. For example, the culture chambers have a space for the formation of cardiac microtissues from a suspension of iPS cardiomyocyte.

The use of the word "a" or "an" when used in conjunction with the term "comprising" in the claims and/or the specification may mean "one," but it is also consistent with the meaning of "one or more," "at least one," and "one or more than one." As used herein "another" may mean at least a second or more.

The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

What we claim is:

1. A bioreactor comprising:
   a modular body defining a first well for engineering a first tissue and a second well for engineering a second tissue;
   a first media inlet flow path in fluid communication with the first well;
   a first media outlet flow path in fluid communication with the first well, wherein a first tissue-specific media is able to be injected into the first well via the first media inlet flow path, and wherein the first tissue-specific media can exit the first well via the first media outlet flow path;
   a second media inlet flow path in fluid communication with the second well;
   a second media outlet flow path in fluid communication with the second well, wherein a second tissue-specific media is able to be injected into the second well via the second media inlet flow path, and wherein the second tissue-specific media can exit the second well via the second media outlet flow path;
   a pair of first pillars, each first pillar having an upper end and a lower end, wherein the upper end is engaged with a first support member such that each first pillar extends downwardly from the first support member along a longitudinal axis with the lower end of each first pillar being disposed in the first well, wherein the pair of first pillars each comprise a central channel to permit fluid communication between the first pillars, and wherein the pair of first pillars are capable of supporting the first tissue and providing a common media to an internal cavity of the first tissue via the central channel, and wherein said common media does not mix with the first tissue-specific media in the first well; and a pair of second pillars, each second pillar having an upper end and a lower end, wherein the upper end is engaged with a second support member such that each second pillar extends downwardly from the second support member along a longitudinal axis with the lower end of each second pillar being disposed in the second well, wherein the lower ends are joined by a horizontal segment, wherein the second pillars and horizontal segment are capable of fluid communication via a central channel in the second pillars and horizontal segment, and wherein at least a portion of each second pillar or the horizontal segment is formed of a permeable membrane thereby permitting fluid access to the second tissue when in contact with the permeable membrane.

2. The bioreactor of claim 1, wherein the central channel of the pair of first pillars is in fluid communication with the central channel of the pair of second pillars via a connecting flow conduit such that the common media can flow between the first and second tissues in the first and second wells, respectively.

3. The bioreactor of claim 1 further comprising electrically conductive material disposed on the lateral side of each of the pair of first pillars.

4. The bioreactor of claim 3, wherein the electrically conductive material is a carbon rod.

5. The bioreactor of claim 3 further comprising an electrical stimulator in electrical communication with the electrically conductive material.

6. The bioreactor of claim 1, wherein the lower end of each first pillar comprises a head, wherein the head comprises a flared end extending perpendicularly from the longitudinal axis, wherein the flared end defines an opening in communication with the central channel of the first pillar, wherein the openings of the flared ends of the pair of first pillars face each other and are aligned vertically and horizontally, wherein the heads of each first pillar provide a support surface for the first tissue, and wherein the opening is in communication with the internal cavity of the first tissue.

7. The bioreactor of claim 6, wherein the flared end has a circular cross-section.

8. The bioreactor of claim 6, wherein the head further comprises a lateral portion extending outwardly in the direction opposite the flared end, and wherein the lateral portion does not contain an opening.

9. The bioreactor of claim 1, wherein the permeable membrane has a permeability of three microns or less.

10. The bioreactor of claim 1, wherein the distance between the pair of first pillars and the distance between the pair of second pillars is each from about 3 mm to about 8 mm.

11. The bioreactor of claim 1, wherein the modular body further comprises one or more additional first wells for engineering additional first tissues and one or more additional second wells for engineering additional second tissues, wherein the one or more additional first wells is in fluid communication with the first media inlet flow path and the first media outlet flow path, and wherein the one or more additional second wells is in fluid communication with the second media inlet flow path and the second media outlet flow path.

12. The bioreactor of claim 1, wherein the modular body further defines a third well for engineering a third tissue;

a third media inlet port providing access to a third media inlet flow path, wherein the third media inlet flow path is in fluid communication with the third well;

a third media outlet flow path in fluid communication with the third well, wherein a third tissue-specific media is able to be injected into the third media inlet port and directed to the third well via the third media inlet flow path, and wherein the third tissue-specific media can exit the third well via the third media outlet path; and a second pair of second pillars extending into the third well, wherein the central channel of the second pair of second pillars is in communication with the central channel of the pair of first pillars and central channel of the pair of second pillars via a connecting flow conduit such that the common media can flow between the first, second, and third tissues in the first, second, and third wells, respectively.

* * * * *